(12) United States Patent
Yahata et al.

(10) Patent No.: US 10,143,406 B2
(45) Date of Patent: Dec. 4, 2018

(54) FEATURE-QUANTITY EXTRACTING APPARATUS

(71) Applicant: CASIO COMPUTER CO., LTD., Shibuya-ku, Tokyo (JP)

(72) Inventors: Takashi Yahata, Hamura (JP); Takao Kanke, Akishima (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 672 days.

(21) Appl. No.: 14/298,024

(22) Filed: Jun. 6, 2014

(65) Prior Publication Data

US 2015/0019171 A1    Jan. 15, 2015

(30) Foreign Application Priority Data

Jul. 11, 2013  (JP) .................................. 2013-145122

(51) Int. Cl.
*H03F 1/26* (2006.01)
*A61B 5/11* (2006.01)

(52) U.S. Cl.
CPC ........... *A61B 5/1118* (2013.01); *A61B 5/1112* (2013.01); *A61B 5/1116* (2013.01); *A61B 5/1123* (2013.01)

(58) Field of Classification Search
CPC ... A61B 5/1118; A61B 5/1123; A61B 5/1116; A61B 5/1112

(Continued)

(56) References Cited

U.S. PATENT DOCUMENTS

| 7,116,943 B2 * | 10/2006 | Sugar | H04L 1/1664 |
| | | | 455/67.11 |
| 7,693,668 B2 * | 4/2010 | Vock | G01P 3/50 |
| | | | 702/44 |

(Continued)

FOREIGN PATENT DOCUMENTS

| JP | 10-113343 | 5/1998 |
| JP | 2006-202350 | 8/2006 |

OTHER PUBLICATIONS

Office Action of Notification of Reasons for Refusal for Japanese Patent Application No. 2013-145122 dated Apr. 28, 2015, 9 pages.

*Primary Examiner* — An Do
(74) *Attorney, Agent, or Firm* — Amin, Turocy & Watson LLP

(57) ABSTRACT

A feature-quantity extracting apparatus is provided, which can calculate a proper feature quantity, by performing a simple calculating operation. The apparatus is provided with a code-string acquiring unit for acquiring code strings for every given period from a series of input data, wherein the code string is an arrangement of codes and the code is given to a value of each piece of input data, a code-string pattern frequency counting unit for counting the number of code-string patterns for every code-string pattern among the code strings acquired by the code-string acquiring unit, wherein the code-string pattern represents a code-string whose codes are arranged in accordance with a given order, and a feature-quantity outputting unit for outputting the number of code-string patterns for every code-string pattern counted by the code-string pattern frequency counting unit as a feature quantity of the series of input data.

3 Claims, 4 Drawing Sheets

(58) Field of Classification Search
USPC .......................................... 702/127, 189, 190
See application file for complete search history.

(56) References Cited

U.S. PATENT DOCUMENTS

| | | | | |
|---|---|---|---|---|
| 2004/0094613 | A1* | 5/2004 | Shiratori | A61B 5/1118 |
| | | | | 235/105 |
| 2004/0249258 | A1* | 12/2004 | Tupin, Jr. | A61B 5/05 |
| | | | | 600/407 |
| 2008/0052045 | A1* | 2/2008 | Brewer | G06F 17/10 |
| | | | | 702/190 |
| 2008/0275348 | A1* | 11/2008 | Catt | A61B 5/1112 |
| | | | | 600/483 |
| 2009/0062628 | A1* | 3/2009 | Yamamoto | A61B 5/08 |
| | | | | 600/301 |
| 2013/0015976 | A1* | 1/2013 | Chang | A61B 5/0002 |
| | | | | 340/573.7 |
| 2014/0128778 | A1* | 5/2014 | Chan | A61B 5/1116 |
| | | | | 600/595 |
| 2015/0054654 | A1* | 2/2015 | Albinali | G08B 21/02 |
| | | | | 340/870.01 |
| 2016/0066864 | A1* | 3/2016 | Frieder | A61B 5/7282 |
| | | | | 600/300 |

\* cited by examiner

FEATURE-QUANTITY EXTRACTING APPARATUS

CROSS-REFERENCE TO RELATED APPLICATION

The present application is based upon and claims the benefit of priority from the prior Japanese Patent Application No. 2013-145122, filed Jul. 11, 2013, the entire contents of which are incorporated herein by reference.

BACKGROUND OF THE INVENTION

1. Field of the Invention

The present invention relates to a feature-quantity extracting apparatus which extract a feature quantity from entered data.

2. Description of the Related Art

Technology is known, in which a device having a built-in acceleration sensor is put on a human body and behavior of the human is estimated based on signal data sent from the acceleration sensor.

When the technology is applied to activity meters, into which pedometers are developed, an activity quantity (METS hours) will be calculated more precisely based on the behavior of the human wearing the active meter. Further, calories consumed in the activity can be calculated from the activity quantity and personal information (height, weight, etc).

In general, the following system is employed as the specific technology for estimating behavior of a human. For example, in the system, various sorts of feature quantities are acquired for every given interval from signal data which is acquired while the human is in some behavior. Meanwhile, feature quantities are acquired from plural humans whose behavior is previously known and the acquired feature quantities are used as supervised learning data. When data is acquired from a sensor while a human is in unknown behavior, a similar feature quantity is calculated from the acquired data. The similar feature quantity is collated with the supervised learning data, whereby the behavior of the human is estimated. More specifically, using the well known classifying method such as AdaBoost and Support Vector Machine (SVM), the system generates a classifier from the feature quantity used as the supervised learning data and stores the classifier in an activity meter. When using the activity meter, the system calculates a feature quantity from data that is output from the sensor while the human is in unknown behavior and enters the calculated feature quantity to the classifier, thereby acquiring a resultant classification.

As conventional technology for estimating the human behavior, the following system is known (for example, refer to Japanese Unexamined Patent Publication No. Hei10-113343). In the system, a measuring device is fit on a human to measure his/her motion and/or behavior, and a feature-quantity extracting unit extracts a feature quantity from a signal representing the motion and/or behavior of the human, and a signal processing unit for confirming human motion and/or behavior compares the extracted feature quantity with reference data, wherein the reference data is previously stored in a database of data representing feature quantities of various sorts of human motions and/or behaviors, whereby the motion and/or behavior of the feature quantity having a highest correlational relationship is output as a classification result.

Generally, in the conventional system, a frequency feature quantity acquired in a time-frequency transform arithmetic processing such as the Fourier transform and Wavelet transform is used as the feature quantity to be calculated from data of the sensor.

SUMMARY OF THE INVENTION

According to one aspect of the invention, there is provided a feature-quantity extracting apparatus which comprises a code-string acquiring unit which acquires code strings for every given period from a series of input data, wherein the code string is an arrangement of codes and the code is given to a value of each piece of input data, a code-string pattern frequency counting unit which counts the number of code-string patterns for every code-string pattern among the code strings acquired by the code-string acquiring unit, wherein the code-string pattern represents a code-string whose codes are arranged in accordance with a given order, and a feature-quantity outputting unit which outputs the number of code-string patterns for every code-string pattern counted by the code-string pattern frequency counting unit as a feature quantity of the series of input data.

DETAILED DESCRIPTION OF THE PREFERRED EMBODIMENTS

Now, the preferred embodiments of the present invention will be described with reference to the accompanying drawings in detail.

Figure 1:
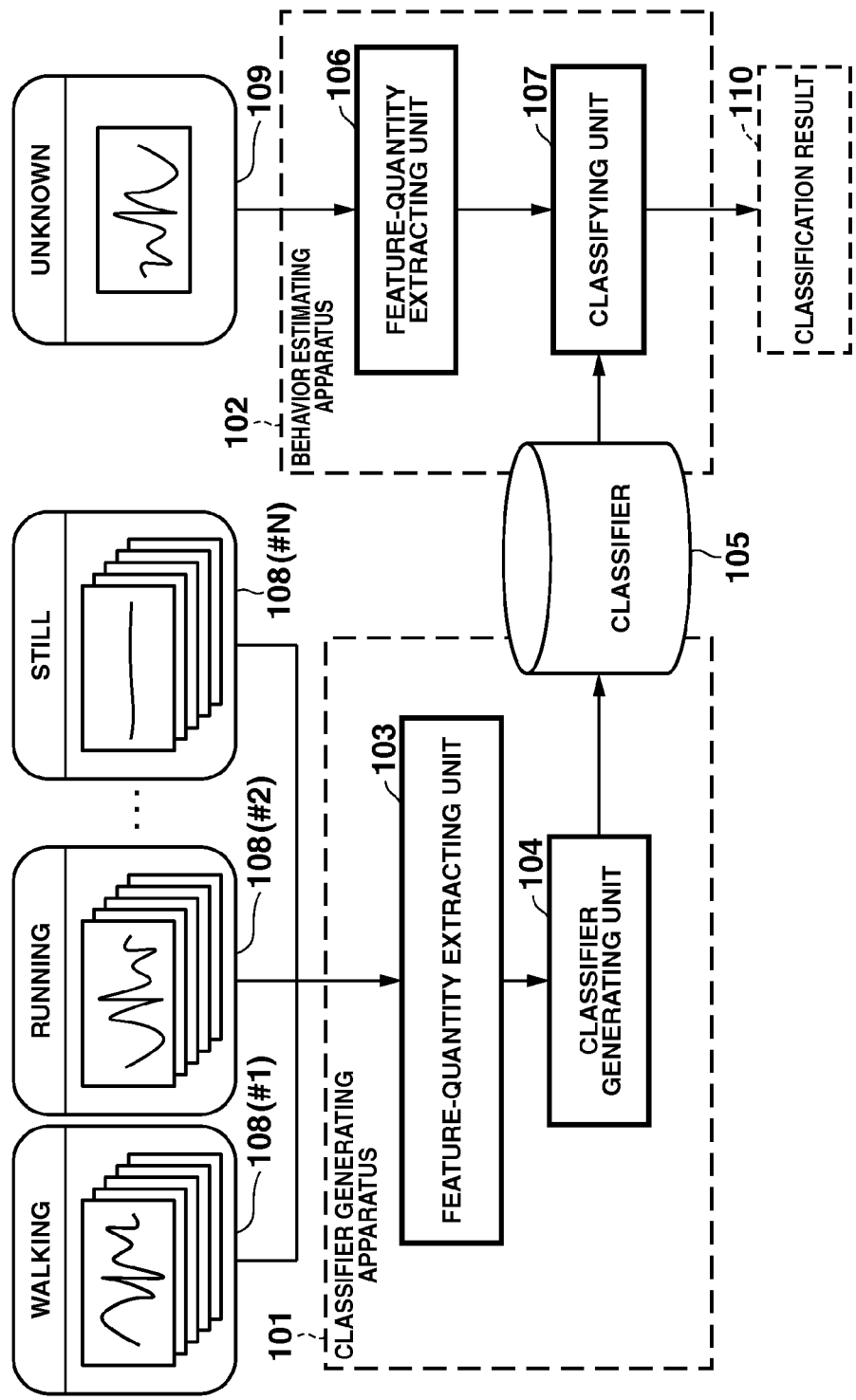
FIG. 1 is a view showing a configuration of a system according to the embodiment of the invention.

FIG. 1 is a view showing a configuration of a system according to the embodiment of the invention.

The system comprises a classifier generating apparatus 101 and a behavior estimating apparatus 102.

The behavior estimating apparatus 102 is, for example, an activity meter, and is attached on a human body for use. Meanwhile, the classifier generating apparatus 101 is, for example, a computer apparatus. Although the details thereof will be described later, for example, the classifier generating apparatus 101, that is, the computer apparatus enters acceleration data recorded in a sensor-data recording device to another classifier generating apparatus 101 as learning data, thereby generating a classifier 105 to be mounted on the behavior estimating apparatus 102. The classifier generating apparatus 101 is used in isolation from the behavior estimating apparatus 102, for example, within manufacturers of the behavior estimating apparatuses 102.

Data from acceleration sensors prepared for respective sorts of activities to be classified is entered to the classifier generating apparatus 101 as plural pieces of learning acceleration data 108 (#1 to #N) as shown in FIG. 1.

A feature-quantity extracting unit 103 mounted on the classifier generating apparatus 101 extracts feature quantities from the acceleration data 108. As the feature quantities of the acceleration data 108, a code-string pattern frequency is proposed and calculated in the present embodiment of the invention in addition to an average and a variance of the acceleration data 108.

A classifier generating unit 104 mounted on the classifier generating apparatus 101 uses classifying algorithms, which are well known as AdaBoost and Support Vector Machines (SVMs), to generate the classifier 105 for the entered feature-quantity data extracted by the feature-quantity extracting unit 103.

The classifier 105 generated by the classifier generating apparatus 101 is supplied from a storage device of the classifier generating apparatus 101 to a storage device of the behavior estimating apparatus 102 through a transportable recording medium and/or a communication network.

The behavior estimating apparatus 102 estimates behavior of a human who puts the apparatus 102 itself on his/her own body in a manner described below.

The acceleration sensor of the behavior estimating apparatus 102 outputs acceleration data 109 of unknown behavior.

A feature-quantity extracting unit 106 mounted on the behavior estimating apparatus 102 extracts feature quantities from the acceleration data 109. The feature quantities from the acceleration data 109 are substantially the same as those extracted by the feature-quantity extracting unit 103 mounted on the classifier generating apparatus 101, and include a code-string pattern/frequency proposed and calculated in the present embodiment of the invention in addition to an average and a variance of the acceleration data 109.

A classifying unit 107 mounted on the behavior estimating apparatus 102 uses the classifier 105 to perform classification of the behavior on the acceleration data 109 and outputs the classification as a classification result 110.

For instance, an activity quantity (METS hours) is calculated based on the classification result 110, and further calories consumed in the activity is calculated from the classification result 110 and personal information (height, weight, etc).

Figure 2:
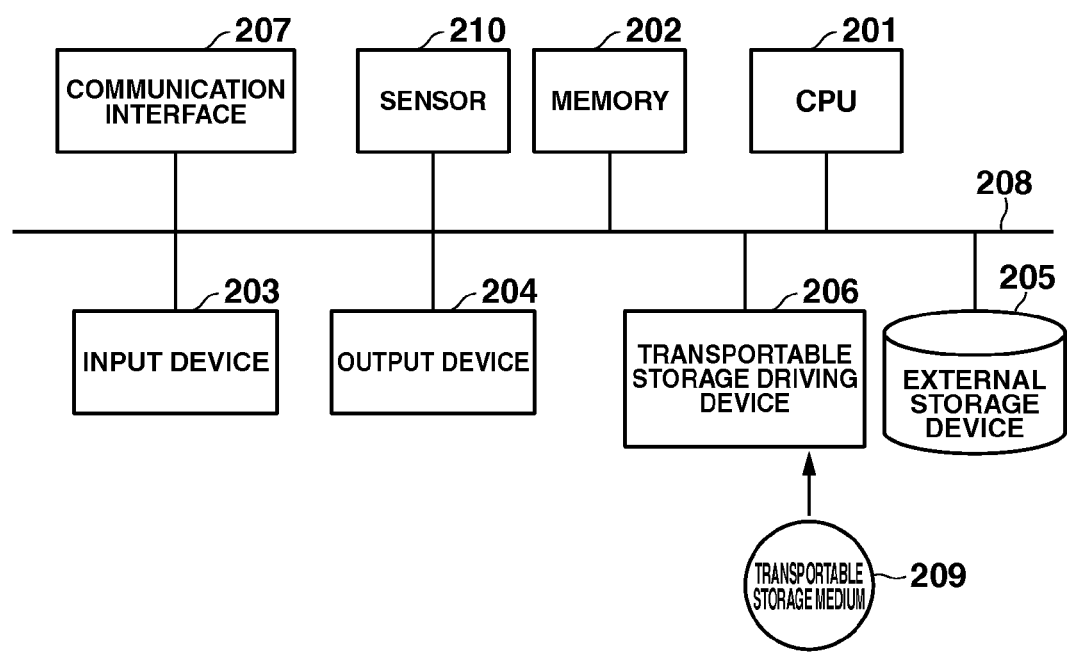
FIG. 2 is a block diagram showing a configuration of hardware according to the embodiment of the invention.

FIG. 2 is a block diagram showing a configuration of hardware according to the embodiment of the invention.

When this hardware configuration is applied to the classifier generating apparatus 101, the hardware will operate as a computer used within the manufacturer. In this case, the computer illustrated in FIG. 2 comprises CPU 201, a memory 202, an external storage device 205 such as a hard disk drive, a transportable storage driving device 206 for receiving a transportable storage medium 209 such as a memory card, and a communication interface 207 to be connected with LAN (Local Area Network) and/or the Internet. These elements are connected with each other through a bus 208. The configuration illustrated in FIG. 2 is one example of the computer that can realize the classifier generating apparatus 101. Such computer is not limited to the configuration illustrated in FIG. 2.

When the hardware configuration illustrated in FIG. 2 is applied to the behavior estimating apparatus 102, the hardware will operate as a transportable compact activity meter manufactured in the manufacturer. The activity meter is attached on a human body for use. In this case, the computer illustrated in FIG. 2 comprises CPU 201, a memory 202 including RAM (Random Access Memory) and ROM (Read Only Memory) for storing a program and the classifier 105 (FIG. 1), an acceleration sensor 210, and input device 203 including operation instructing buttons, and an output device 204 such as a compact liquid crystal displaying device. These elements are connected with each other through the bus 208. The external storage device 205, the transportable storage driving device 206 and the communication interface 207 are not essential elements for the computer. The configuration illustrated in FIG. 2 is one example of the computer that can realize the behavior estimating apparatus 102. Such computer is not limited to the configuration illustrated in FIG. 2.

CPU 201 controls the whole operation of the computer. The memory 202 serves as RAM for temporarily storing a control program and data when the program is executed and data is updated. When the hardware illustrated in FIG. 2 functions as the behavior estimating apparatus 102, the memory 202 serves as ROM for storing the control program and the classifier 105 (FIG. 1).

CPU 201 reads onto the memory 202 and executes the programs for realizing the functions of the classifier generating apparatus 101 and the behavior estimating apparatus 102, both shown in FIG. 1, thereby controlling the whole operation of the computer. In particular, the classifier generating apparatus 101 and/or the behavior estimating apparatus 102 in the present embodiment are realized by performing processes in accordance with a flow chart of FIG. 3. CPU 201 executes the program having the function of the feature-quantity extracting unit 103 mounted on the classifier generating apparatus 101 or the function of the feature-quantity extracting unit 106 mounted on the behavior estimating apparatus 102, both shown in FIG. 1, thereby performing a feature-quantity acquiring process. It is possible to record the program on the external storage device 205 and the transportable storage medium 209 and to distribute the program recorded on the storage device 205 and/or the storage medium 209, and further, it is possible to receive the program from the network through the communication interface 207. Further, it is also possible for the manufacturer to previously store the program on ROM and supply the program stored on said ROM.

Figure 3:
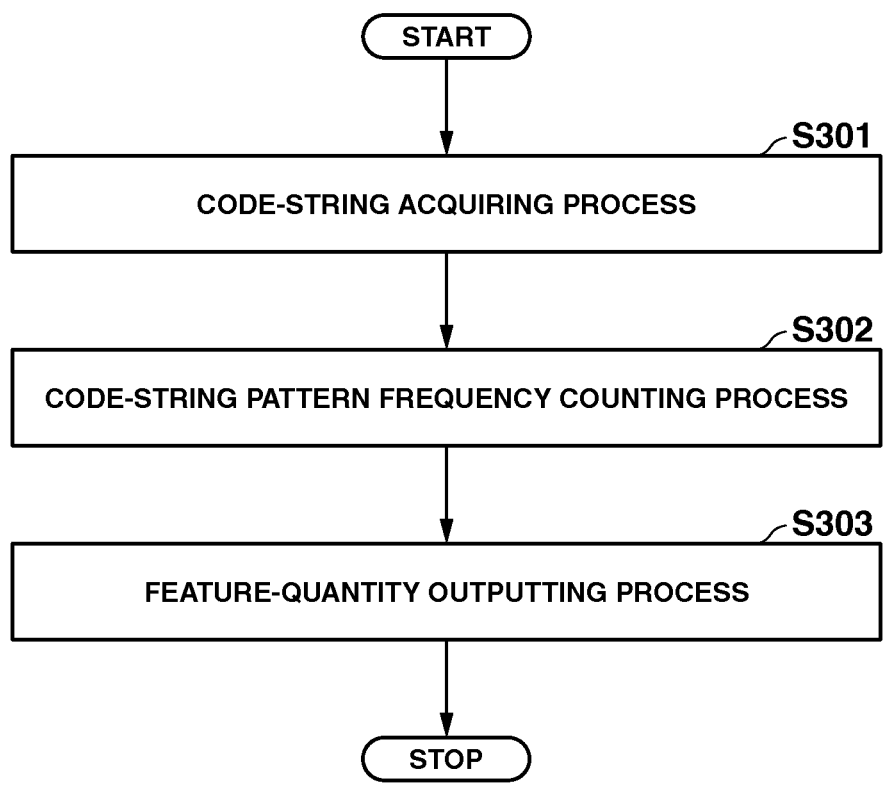
FIG. 3 is a flow chart of a feature-quantity extracting process performed in the embodiment of the invention.

FIG. 3 is a flow chart of the feature-quantity extracting process performed by the feature-quantity extracting unit 103 of the classifier generating apparatus 101 and/or the feature-quantity extracting unit 106 of the behavior estimating apparatus 102.

In FIG. 2, continuous time-series data, that is, acceleration data is entered to CPU 201 from the acceleration sensor 210, and strings of codes (code strings) are acquired for every given period from the entered continuous time-series data (acceleration data), wherein the codes represent values of respective pieces of entered data (function of a code-string acquiring unit) (step S301 in FIG. 3).

A frequency of code strings acquired at step S301 is counted for every pattern (function of a code-string pattern/frequency counting unit) (step S302).

The frequency of code strings that has been counted for every pattern at step S302 is output as a feature quantity corresponding to the acceleration data (function of a feature-quantity outputting unit) (step S303).

Hereinafter, the feature-quantity acquiring process illustrated by the flow chart of FIG. 3 will be described in detail.

In the code-string acquiring process at step S301 in FIG. 3, the following operations will be performed.

Figure 4:
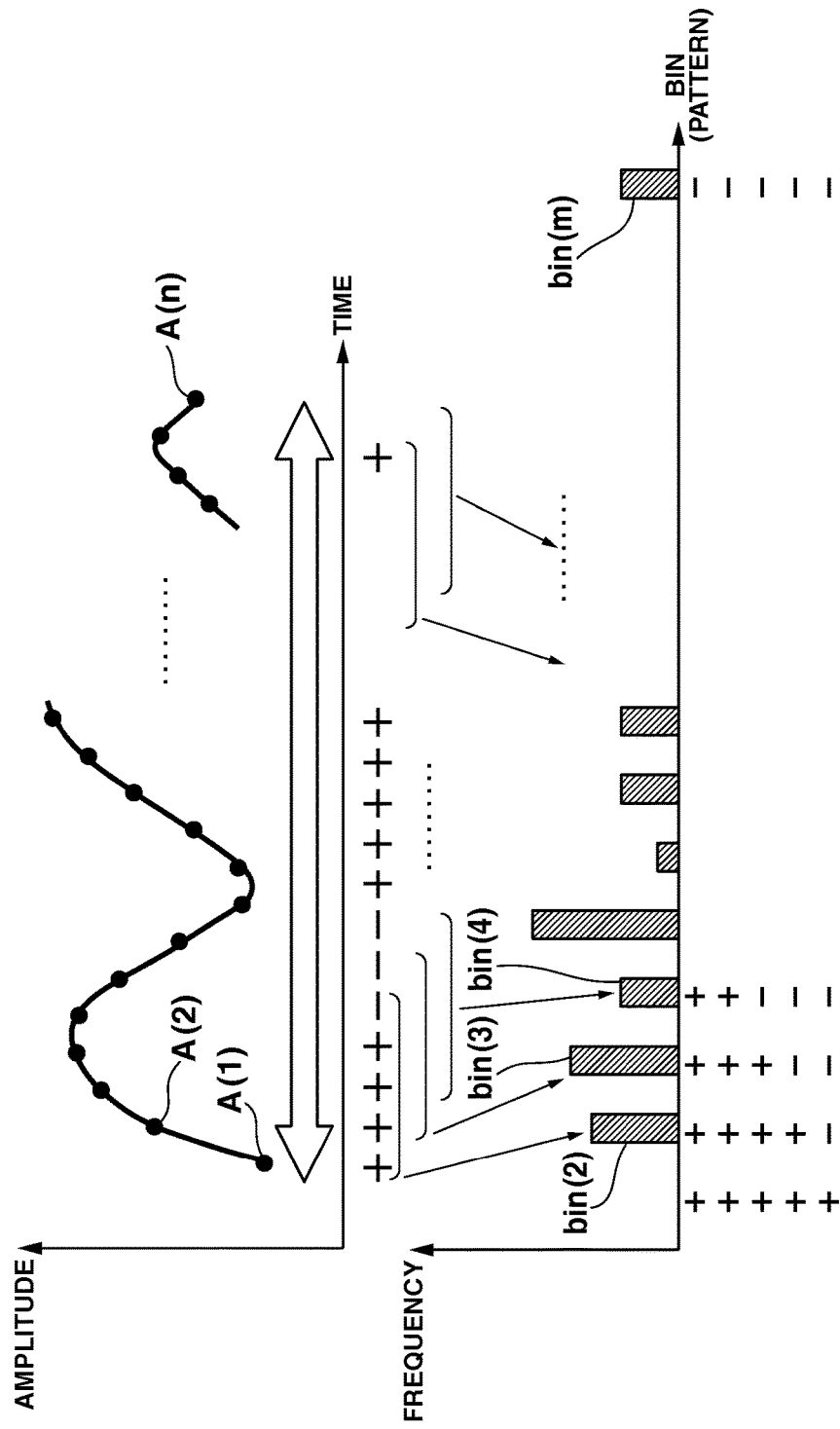
FIG. 4 is a view for explaining operations executed in the feature-quantity extracting process.

As shown in upper graph of FIG. 4, x-components (n pieces: $A(1)$ to $A(n)$) of the time-series acceleration data "A" of the acceleration sensor 210 are acquired for every given period, where each given period is, for example, about several seconds.

Difference data "D" of the time-series acceleration data "A" is calculated by the following equation:

$$D(k) = A(k+1) - A(k) \quad (1 \le k \le n-1)$$

When the calculated difference data "D" is a positive value, then a code of "+" is given to D(k), and when the calculated difference data "D" is a negative value, then a code of "−" is given to D(k).

Out of plural pieces of difference data "D" calculated in the above manner, "p" pieces of difference data "D" (from the first data successively to "p"-th data) are apposed in a line and then their codes are also apposed in a line. For example, when "p" is to be 5, then $D(1), D(2), D(3), D(4), D(5) = ++++-$ Then, the apposed plural pieces of data are slid in time and their codes are apposed in the same manner.

$D(2), D(3), D(4), D(5), D(6) = +++--$

The above operation is repeatedly performed as far as the difference data "D" is left.

In the code-string pattern frequency counting process at step S302 in FIG. 3, the following operations will be performed.

The number of arrangements of the codes (code strings) is given by $m=2^P$ (the P-th power of 2). In the case of P=5, $m=2^5=32$. The frequency of each of the code arrangements (the frequency of each of the code-string patterns) acquired in the above code-string pattern frequency counting process is illustrated in a histogram as indicated by arrows in FIG. 4.

For instance, as illustrated in the histogram shown in lower graph of FIG. 4, every time the code-string pattern of "++++−" appears, the frequency or the number of code-string patterns of "++++−" falling into bin(2) is incremented by one. Also, every time the code-string pattern of "+++−−" appears, the frequency or the number of code-string patterns of "+++−−" falling into bin(3) is incremented by one. Further, every time the code-string pattern of "++−−−" appears, the frequency or the number of code-string patterns of "++−−−" falling into bin(4) is incremented by one.

In the feature-quantity outputting process at step S303, the frequency, that is, the number of each of the P-th power of 2 pieces of bins, from bin(1) to bin(m), as calculated above, is output as a feature quantity corresponding to the acceleration data "A".

When the feature-quantity extracting process is subjected to an operation of the feature-quantity extracting unit 103 of the classifier generating apparatus 101 and an operation of the feature-quantity extracting unit 106 of the behavior estimating apparatus 102, both shown in FIG. 1, an appropriate feature quantity corresponding to waveform information of the difference data can be calculated in a more simple difference calculating process and histogram counting process, without performing a complex arithmetic processing such as a time-frequency conversion processing.

In the above embodiment, the case of P=5 has been described, but any pieces ("P") of data can be employed.

Further in the above embodiment, the codes of respective pieces of data are simply apposed in a line. It is possible to classify the code "+" into two classes, "1+" and "2+", and also the code "−" into two classes, "1−", and "2−", depending on the absolute amplitudes of respective pieces of acceleration data "A" and to appose these four sorts of codes, "1+", "2+", "1−", and "2−" in a line. In this case, the number of arrangements of the code strings will be 256 (the fifth power of four) and 256 feature quantities have been acquired. The codes can be classified into any number of sorts.

The data to be processed for acquiring the feature quantity according to the present invention is not limited to the data from the acceleration sensor and/or the time-series data. Any series of one-dimensional continuous data can be used for acquiring the feature quantity according to the present invention.

In the above described embodiments of the invention, the time-oriented codes are apposed continuously but the plural codes can be apposed every other one or every third one. Further, the codes can be apposed in any manner.

Although specific embodiments of the invention have been described in the foregoing detailed description, it will be understood that the invention is not limited to the particular embodiments described herein, modifications and rearrangements may be made to the disclosed embodiments while remaining within the scope of the invention as defined by the following claims. It is intended to include all such modifications and rearrangements in the following claims and their equivalents.

What is claimed is:

1. A feature-quantity extracting apparatus having a processor, which apparatus receives time-series data from a sensor and extracts a feature quantity of the received data without performing a time-frequency conversion process on the received data, wherein the processor performs a process comprising:

a code information acquiring process, executed by the processor, for obtaining plural pieces of time-series data A(1) to A(n) (n: an integer) each having a predetermined time period from the received time-series data; obtaining difference data D from the plural time-series data A(1) to A(n) by performing a following equation $D(k)=A(k+1)-A(k)(1 \le k \le n-1)$;

and, giving a code of "+" to the difference data D when the difference data D has a positive value, and giving a code of "−" to the difference data D when the difference data D has a negative value, thereby acquiring plural pieces of code information with the code of "+" or "−" given, which are sequential time serially beginning from a predetermined time a code-information string acquiring process, executed by the processor, for picking out P (P: an integer smaller than "n") pieces of code information which are sequential in time from a piece of code information as a code information string from the acquired plural pieces of code information which are sequential time serially starting from a predetermined time, and then sequentially picking out another P pieces of code information which are sequential in time starting from a piece of code information shifted by 1 in a time axis as another code information string from the acquired plural pieces of code information, thereby picking out plural code information strings each containing P pieces of code information, wherein each of the plural code information strings comprises P elements wherein each of the of the P elements are either "+" or "−";

a histogram representing process, executed by the processor, for counting a frequency of a pattern indicated by the arranged codes of "+" and/or "−" included in the code information string, wherein each plural code information string are grouped with other plural code information strings that have a same number of "−" in the plural code information strings, and a histogram is formed where the x axis represents difference groupings of plural code information strings based on the number of "−" in the plural code information string, and the y axis represents a frequency of occurrence of each plural code information string, and representing the counted frequency of each of the plural code information strings in a histogram;
a feature-quantity extracting process, executed by the processor, for extracting the histogram as the feature quantity of the received data; and
displaying the histogram and feature quantity on a liquid crystal display device.

2. A feature-quantity extracting method for receiving time-series data received from a sensor and extracting a feature-quantity of the received data without performing a time-frequency conversion process on the received data, the method comprising the steps of:
(a) obtaining, by a processor, plural pieces of time-series data A(1) to A(n) (n: an integer) each having a predetermined time period from the received time-series data;
(b) obtaining, by the processor, difference data D from the plural time-series data A(1) to A(n) by performing a following equation $$D(k)=A(k+1)-A(k)(1 \leq k \leq n-1);$$

(c) giving, by the processor, a code of "+" to the difference data D when the difference data D has a positive value, and giving a code of "−" to the difference data D when the difference data D has a negative value, thereby acquiring plural pieces of code information with the code of "+" or "−" given, which are sequential time serially beginning from a predetermined time;
(d) picking, by the processor, out P (P: an integer smaller than "n") pieces of code information which are sequential in time from a piece of code information as a code information string from the acquired plural pieces of code information which are sequential time serially starting from a predetermined time, and then sequentially picking out another P pieces of code information which are sequential in time from a piece of code information shifted by 1 in a time axis as another code information string from the acquired plural pieces of code information, thereby picking out plural code information strings each containing P pieces of code information, wherein each of the plural code information strings comprises P elements wherein each of the of the P elements are either "+" or "−";
(e) counting, by the processor, a frequency of a pattern indicated by the arranged codes of "+" and/or "−" included in the code information string, wherein each plural code information string are grouped with other plural code information strings that have a same number of "−" in the plural code information strings, and a histogram is formed where the x axis represents difference groupings of plural code information strings based on the number of "−" in the plural code information string, and the y axis represents a frequency of occurrence of each plural code information string, and representing the counted frequency of each of the plural code information strings in a histogram;
(f) extracting, by the processor, the histogram as the feature quantity of the received data; and
displaying the histogram and feature quantity on a liquid crystal display device.

3. A non-transitory computer-readable storage medium with an executable program stored thereon, wherein a computer is mounted on a feature-quantity extracting apparatus which receives time-series data from a sensor and extracts a feature quantity of the received data without performing a time-frequency conversion process on the received data, the program, when installed on the computer, making the computer perform a process comprising:
a code information acquiring process, executed by a processor, for obtaining plural pieces of time-series data A(1) to A(n) (n: an integer) each having a predetermined time period from the received time-series data; obtaining difference data D from the plural time-series data A(1) to A(n) by performing a following equation $$D(k)=A(k+1)-A(k)(1 \leq k \leq n-1);$$

and, giving a code of "+" to the difference data D when the difference data D has a positive value, and giving a code of "−" to the difference data D when the difference data D has a negative value, thereby acquiring plural pieces of code information with the code of "+" or "−" given, which are sequential time serially beginning from a predetermined time;
a code-information string acquiring process, executed by the processor, for picking out P (P: an integer smaller than "n") pieces of code information which are sequential in time from a piece of code information as a code information string from the acquired plural pieces of code information which are sequential time serially starting from a predetermined time, and then sequentially picking out another P pieces of code information which are sequential in time starting from a piece of code information shifted by 1 in a time axis as another code information string from the acquired plural pieces of code information, thereby picking out plural code information strings each containing P pieces of code information, wherein each of the plural code information strings comprises P elements wherein each of the of the P elements are either "+" or "−";
a histogram representing process, executed by the processor, for counting a frequency of a pattern indicated by the arranged codes of "+" and/or "−" included in the code information string, wherein each plural code information string are grouped with other plural code information strings that have a same number of "−" in the plural code information strings, and a histogram is formed where the x axis represents difference groupings of plural code information strings based on the number of "−" in the plural code information string, and the y axis represents a frequency of occurrence of each plural code information string, and representing the counted frequency of each of the plural code information strings in a histogram;
a feature-quantity extracting process, executed by the processor, for extracting the histogram as the feature quantity of the received data; and
displaying the histogram and feature quantity on a liquid crystal display device.

* * * * *